(12) United States Patent
Guggenberger et al.

(10) Patent No.: US 12,167,879 B2
(45) Date of Patent: Dec. 17, 2024

(54) NAVIGATION-ENABLED CRYOABLATION SYSTEM WITH INDIRECT DEVICE TRACKING

(71) Applicant: Boston Scientific Scimed Inc., Maple Grove, MN (US)

(72) Inventors: Kurt Edmund Guggenberger, North Andover, MA (US); Eugene J. Jung, Jr., San Diego, CA (US); Steven A. Kubow, Hugo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 340 days.

(21) Appl. No.: 17/206,499

(22) Filed: Mar. 19, 2021

(65) Prior Publication Data

US 2021/0290283 A1   Sep. 23, 2021

Related U.S. Application Data

(60) Provisional application No. 62/991,981, filed on Mar. 19, 2020.

(51) Int. Cl.
| | |
|---|---|
| *A61B 18/02* | (2006.01) |
| *A61B 34/20* | (2016.01) |
| *A61B 18/00* | (2006.01) |
| *A61B 90/00* | (2016.01) |

(52) U.S. Cl.
CPC .............. *A61B 18/02* (2013.01); *A61B 34/20* (2016.02); *A61B 2018/0022* (2013.01); *A61B 2018/00357* (2013.01); *A61B 2018/00577* (2013.01); *A61B 2018/00839* (2013.01); *A61B 2018/0091* (2013.01); *A61B 2018/0212* (2013.01); *A61B 2034/2051* (2016.02); *A61B 2034/2055* (2016.02); *A61B 2034/2059* (2016.02); *A61B 2090/3983* (2016.02)

(58) Field of Classification Search
CPC . A61B 18/02; A61B 34/20; A61B 2034/2059; A61B 2034/2055; A61B 2034/2051; A61B 2018/0022; A61B 2018/00577; A61B 2018/0091
See application file for complete search history.

(56) References Cited

U.S. PATENT DOCUMENTS

| | | | |
|---|---|---|---|
| 2002/0183730 A1* | 12/2002 | Reu ........................ | A61B 18/02 606/21 |
| 2005/0033135 A1* | 2/2005 | Govari ................... | A61B 5/053 600/374 |

(Continued)

*Primary Examiner* — Daniel W Fowler
(74) *Attorney, Agent, or Firm* — Nelson Mullins Riley & Scarborough LLP

(57) ABSTRACT

A cryoablation catheter system comprises a cryoablation catheter having a shaft, a guidewire lumen member and an expandable balloon attached to the shaft and the guidewire lumen member, and an auxiliary device configured for use in combination with the cryoablation catheter, the auxiliary device including a location sensor configured to provide a sensor output indicative of a location of the location sensor within a localization volume responsive to a localization field. A user-accessible relative position indicator is located on one or both of the cryoablation catheter and the auxiliary device and is configured to provide an indication of a relative position of the cryoballoon and the location sensor.

19 Claims, 9 Drawing Sheets

(56) References Cited

U.S. PATENT DOCUMENTS

| | | | |
|---|---|---|---|
| 2005/0171522 A1* | 8/2005 | Christopherson | A61B 18/1477 |
| | | | 606/41 |
| 2007/0179378 A1* | 8/2007 | Boese | A61B 5/283 |
| | | | 600/407 |
| 2008/0275458 A1* | 11/2008 | Bleich | A61B 17/3401 |
| | | | 606/103 |
| 2016/0015444 A1* | 1/2016 | Wittenberger | A61B 18/02 |
| | | | 606/21 |
| 2017/0079708 A1* | 3/2017 | Gilbert | A61B 18/1206 |
| 2017/0281266 A1* | 10/2017 | Slatkine | A61B 18/14 |
| 2018/0185099 A1* | 7/2018 | Kottenstette | G01B 11/002 |
| 2018/0214215 A1* | 8/2018 | Leo | A61B 5/283 |
| 2018/0256263 A1* | 9/2018 | Krimsky | A61B 5/065 |
| 2019/0183372 A1* | 6/2019 | Ruppersberg | A61B 5/6858 |

* cited by examiner

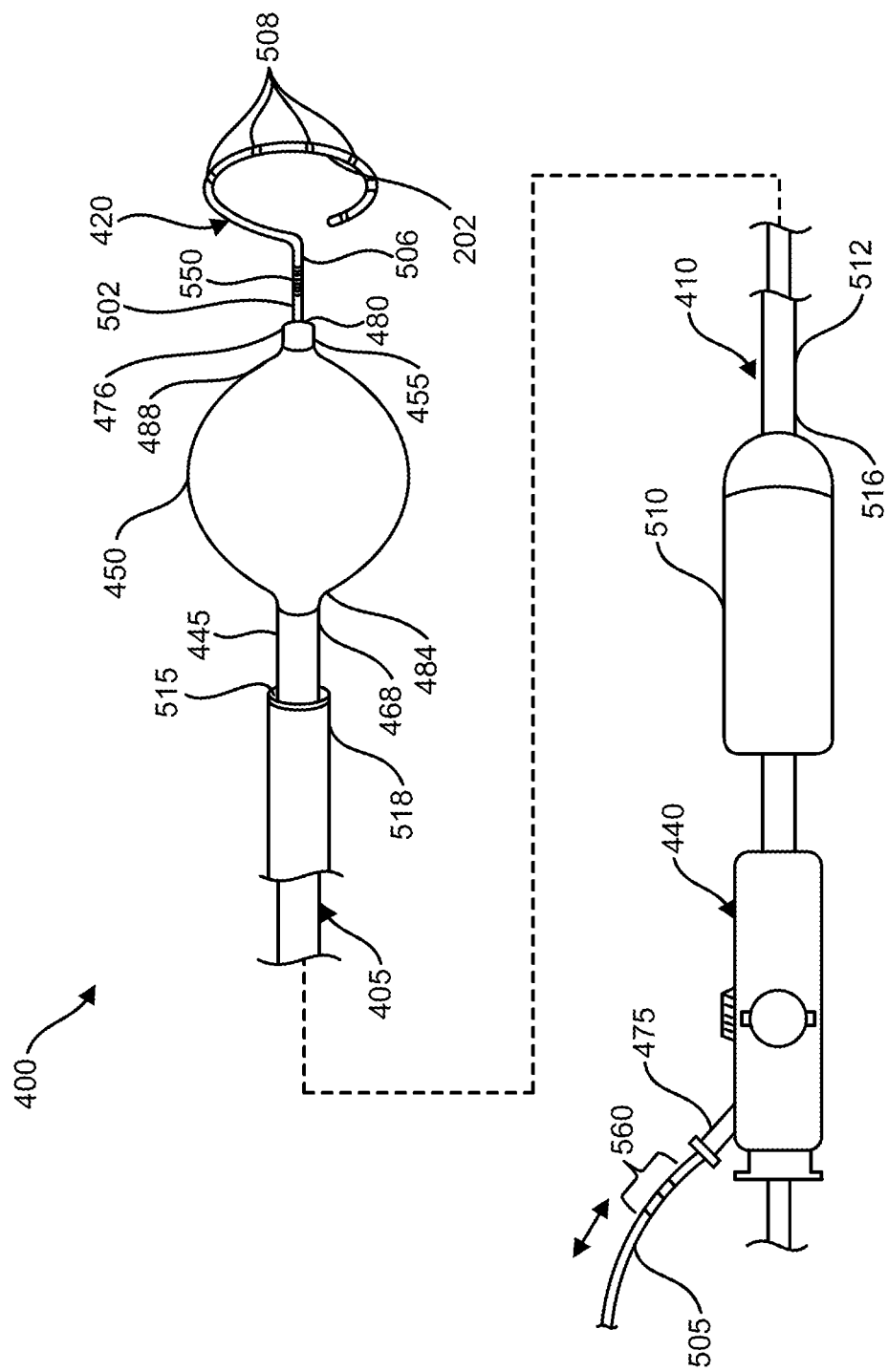

NAVIGATION-ENABLED CRYOABLATION SYSTEM WITH INDIRECT DEVICE TRACKING

CROSS REFERENCE TO RELATED APPLICATION

The application claims priority to Provisional Application No. 62/991,981, filed Mar. 19, 2020, which is herein incorporated by reference in its entirety.

TECHNICAL FIELD

The present disclosure relates to electrophysiology devices and methods. More specifically, the disclosure relates to devices and methods for tracking and displaying the location of a cryoablation catheter within a cardiac chamber of interest.

BACKGROUND

A variety of systems, methods, and devices can be used to spatially track and provide graphical representations of medical devices within patient anatomical chambers such as the left atrium for treating cardiac arrythmias, e.g., atrial fibrillation (AF). Tracking systems can use externally generated localization fields that are sensed by at least one sensor in the tracked medical device. The localization fields provide a fixed frame of reference within a localization volume, and the tracking sensor senses the localization fields to determine the location and, in some cases, orientation of the sensor in relation to the fixed frame of reference. In some cases, the location of the tracked medical device can be used in cardiac mapping systems to generate high-resolution three-dimensional electroanatomical maps of the left atrium (or other cardiac chambers of interest) to aid in diagnosing and treating cardiac arrythmias.

In the earliest stages of AF, a common treatment strategy involves ablating the tissue proximate the ostia of the pulmonary vein(s) so as to bock conduction of arrhythmogenic electrical signals to the left atrial chamber of the heart. Such ablation procedures are known in the art as pulmonary vein isolation (PVI) procedures. PVI can be accomplished using balloon cryotherapy, wherein a cryoballoon of a cryoablation catheter is positioned in contact with the tissue to be ablated, i.e., the tissue proximate the pulmonary vein ostia. Recently, the use of balloon cryotherapy procedures to treat AF has increased. In part, this stems from ease of use, shorter procedure times, and improved patient outcomes.

Incorporation of tracking sensors into conventional cryoablation catheters is complicated by the structural design such devices, which has, to date, precluded the integration of cryoablation technologies with electroanatomical mapping systems.

SUMMARY

In Example 1, a cryoablation catheter system comprising a cryoablation catheter, an auxiliary device and a relative position indicator. The cryoablation catheter comprises a handle, a tubular shaft, a guidewire lumen member and an expandable cryoballoon. The shaft has a shaft proximal end and an opposite shaft distal end, the shaft including a shaft lumen extending between the shaft proximal end and the shaft distal end, the shaft proximal end being coupled to the handle. The guidewire lumen member extends within the shaft lumen and has a guidewire lumen member proximal end and an opposite guidewire lumen member distal end disposed distally of the shaft distal end, the guidewire lumen member having a guidewire lumen extending between the guidewire lumen member proximal end and the guidewire lumen member distal end. The cryoballoon has a proximal portion attached to the shaft distal end and a distal portion attached to the guidewire lumen member distal end. The auxiliary device is configured for use in combination with the cryoablation catheter, the auxiliary device including a location sensor configured to provide a sensor output indicative of a location of the location sensor within a localization volume responsive to a localization field. The relative position indicator is located on one or both of the cryoablation catheter and the auxiliary device configured to provide an indication of a relative position of the cryoballoon and the location sensor.

In Example 2, the cryoablation catheter system of Example 1, further comprising a locking element on one or both of the cryoablation catheter and the auxiliary device configured to selectively fix a position of the cryoballoon catheter relative to the auxiliary device.

In Example 3, the cryoablation catheter system of either of Examples 1 or 2, wherein the relative position indicator is one or more fiducial markers on one or both of the cryoballoon catheter and the auxiliary device.

In Example 4, the cryoablation catheter system of Example 3, wherein the fiducial markers are visible to a user.

In Example 5, the cryoablation catheter system of Example 3, wherein the one or more fiducial markers are located on the auxiliary device, and wherein the cryoablation catheter further comprises a fiducial sensor configured to sense and provide an output indicative of a position of the one or more fiducial markers relative to the fiducial position sensor.

In Example 6, the cryoablation catheter system of Example 5, wherein the fiducial sensor is positioned within the handle of the cryoablation catheter.

In Example 7, the cryoablation catheter system of either of Examples 5 or 6, wherein the fiducial sensor is an optical sensor or an electromechanical sensor.

In Example 8, the cryoablation catheter system of any of Examples 2-7, wherein the locking element is a mechanical locking element configured to secure the cryoablation catheter and the auxiliary device in a fixed position relative to one another.

In Example 9, the cryoablation catheter system of any of Examples 1-8, wherein the auxiliary device is a mapping catheter slidably disposed within the guidewire lumen, the mapping catheter including a mapping catheter distal end portion extending distally of the guidewire lumen member distal end and having a plurality of sensing electrodes.

In Example 10, the cryoablation catheter system of any of Examples 1-8, wherein the auxiliary device is an introducer sheath having a sheath lumen configured to slidably receive the cryoablation catheter for deployment within an anatomical chamber of interest.

In Example 11, the cryoablation catheter system of any of Examples 1-10, wherein the location sensor is an electrode and the localization field is an electric field, and wherein the sensor output is a voltage sensed by the electrode when disposed within the electric field.

In Example 12, the cryoablation catheter system of any of Examples 1-10, wherein the location sensor is a magnetic field sensor and the localization field is a magnetic field generated by a field generator of an electroanatomical mapping system.

In Example 13, an electrophysiology system comprising the cryoablation catheter system of any of Examples 1-10, and an electroanatomical mapping system comprising a localization field generator configured to generate the localization field, a navigation and mapping controller configured to determine the location of the location sensor within the localization field and to generate a graphical representation of the cryoballoon superimposed on a three-dimensional rendering of an anatomical chamber when positioned therein based on the location of the location sensor within the localization field.

In Example 14, the electrophysiology system of Example 12, wherein the location sensor is a magnetic field sensor, the localization field generator is a magnetic field generator, and the localization field is a magnetic field generated by the magnetic field generator.

In Example 15, the electrophysiology system of Example 12, wherein the localization field is an electric field, the localization field generator is an electric field generator, and the location sensor is an electrode, and wherein the sensor output is a voltage sensed by the electrode when disposed within the electric field.

In Example 16, a cryoablation catheter system comprising a cryoablation catheter, an auxiliary device and a relative position indicator. The cryoablation catheter comprises a handle, a tubular shaft, a guidewire lumen member and an expandable cryoballoon. The shaft has a shaft proximal end and an opposite shaft distal end, the shaft being defined by a tubular shaft wall forming a shaft lumen extending between the shaft proximal end and the shaft distal end, the shaft proximal end being coupled to and extending distally from the handle. The guidewire lumen member extends within the shaft lumen and has a guidewire lumen member proximal end and an opposite guidewire lumen member distal end disposed distally of the shaft distal end, the guidewire lumen member being defined by a tubular guidewire lumen member wall forming a guidewire lumen extending between the guidewire lumen member proximal end and the guidewire lumen member distal end. The cryoballoon has a proximal portion attached to the shaft distal end and a distal portion attached to the guidewire lumen member distal end. The auxiliary device is configured for use in combination with the cryoablation catheter, the auxiliary device including a location sensor configured to provide a sensor output indicative of a location of the location sensor within a localization volume responsive to a localization field. The relative position indicator is located on one or both of the cryoablation catheter and the auxiliary device configured to provide an indication of a relative position of the cryoballoon and the location sensor.

In Example 17, the cryoablation catheter system of Example 16, wherein the relative position indicator is one or more fiducial markers on one or both of the cryoballoon catheter and the auxiliary device.

In Example 18, the cryoablation catheter system of Example 17, wherein the fiducial markers are visible to a user.

In Example 19, the cryoablation catheter system of Example 17, wherein the one or more fiducial markers are located on the auxiliary device, and wherein the cryoablation catheter further comprises a fiducial sensor configured to sense and provide an output indicative of a position of the one or more fiducial markers relative to the fiducial position sensor.

In Example 20, the cryoablation catheter system of Example 19, wherein the fiducial sensor is positioned within the handle of the cryoablation catheter.

In Example 21, the cryoablation catheter system of Example 20, wherein the fiducial sensor is an optical sensor or an electromechanical sensor.

In Example 22, the cryoablation catheter system of Example 16, further comprising a locking element on one or both of the cryoablation catheter and the auxiliary device configured to selectively fix a position of the cryoballoon catheter relative to the auxiliary device.

In Example 23, the cryoablation catheter system of Example 22, wherein the locking element is a mechanical locking element configured to secure the cryoablation catheter and the auxiliary device in a fixed position relative to one another.

In Example 24, the cryoablation catheter system of Example 16, wherein the auxiliary device is a mapping catheter slidably disposed within the guidewire lumen, the mapping catheter including a mapping catheter distal end portion extending distally of the guidewire lumen member distal end and having a plurality of sensing electrodes.

In Example 25, the cryoablation catheter system of Example 16, wherein the auxiliary device is an introducer sheath having a sheath lumen configured to slidably receive the cryoablation catheter for deployment within an anatomical chamber of interest.

In Example 26, the cryoablation catheter system of Example 16, wherein the location sensor is an electrode and the localization field is an electric field, and wherein the sensor output is a voltage sensed by the electrode when disposed within the electric field.

In Example 27, the cryoablation catheter system of Example 16, wherein the location sensor is a magnetic field sensor and the localization field is a magnetic field generated by a field generator of a navigation subsystem.

In Example 28, an electrophysiology system comprising a cryoablation catheter, an auxiliary device, a relative position indicator and an electroanatomical mapping system. The cryoablation catheter comprises a handle, a tubular shaft, a guidewire lumen member and an expandable cryoballoon. The shaft has a shaft proximal end and an opposite shaft distal end, the shaft being defined by a tubular shaft wall forming a shaft lumen extending between the shaft proximal end and the shaft distal end, the shaft proximal end being coupled to and extending distally from the handle. The guidewire lumen member extends within the shaft lumen and having a guidewire lumen member proximal end and an opposite guidewire lumen member distal end disposed distally of the shaft distal end, the guidewire lumen member being defined by a tubular guidewire lumen member wall forming a guidewire lumen extending between the guidewire lumen member proximal end and the guidewire lumen member distal end. The cryoballoon has a proximal portion attached to the shaft distal end and a distal portion attached to the guidewire lumen member distal end. The auxiliary device is configured for use in combination with the cryoablation catheter, the auxiliary device including a location sensor configured to provide a sensor output indicative of a location of the location sensor within a localization volume responsive to a localization field. The relative position indicator is located on one or both of the cryoablation catheter and the auxiliary device configured to provide an indication of a relative position of the cryoballoon and the location sensor. The electroanatomical mapping system comprises a localization field generator configured to generate the localization field, and a navigation and mapping controller configured to determine the location of the location sensor within the localization field and to generate a graphical representation of the cryoballoon superimposed on a three-dimensional rendering of an anatomical chamber when positioned therein based on the location of the location sensor within the localization field.

In Example 29, the electrophysiology system of Example 28, wherein the relative position indicator is one or more fiducial markers on one or both of the cryoballoon catheter and the auxiliary device.

In Example 30, the electrophysiology system of Example 29, wherein the one or more fiducial markers are located on the auxiliary device, and wherein the cryoablation catheter further comprises a fiducial sensor configured to sense and provide an output indicative of a position of the one or more fiducial markers relative to the fiducial position sensor.

In Example 31, the electrophysiology system of Example 30, further comprising a locking element on one or both of the cryoablation catheter and the auxiliary device configured to selectively fix a position of the cryoballoon catheter relative to the auxiliary device.

In Example 32, an electrophysiology method comprising generating a localization field using a localization field generator, determining, by a navigation and mapping controller, a location of a location sensor disposed within the localization field on an auxiliary device operatively coupled to a cryoablation catheter having a cryoballoon, determining a location of the cryoballoon relative to the location sensor based on a relative position indicator on one or both of the cryoablation catheter and the auxiliary device, and generating a graphical representation of the cryoballoon superimposed on a three-dimensional rendering of a cardiac chamber located within the localization field based on the determined position of the cryoballoon relative to the location sensor.

In Example 33, the method of Example 32, wherein the relative position indicator includes one or more fiducial markers on one or both of the auxiliary device and the cryoablation catheter.

In Example 34, the method of Example 33, further comprising locking the position of the cryoablation catheter relative to the auxiliary device using a locking element.

In Example 35 the method of Example 33, wherein the cryoablation catheter includes a fiducial sensor, and wherein determining the location of the cryoballoon relative to the location sensor includes sensing a position of the fiducial markers.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIGS. 4A-4D are schematic illustrations of a portion of the cryoablation catheter system of FIG. 1 according to additional alternative embodiments.

Figure 1:
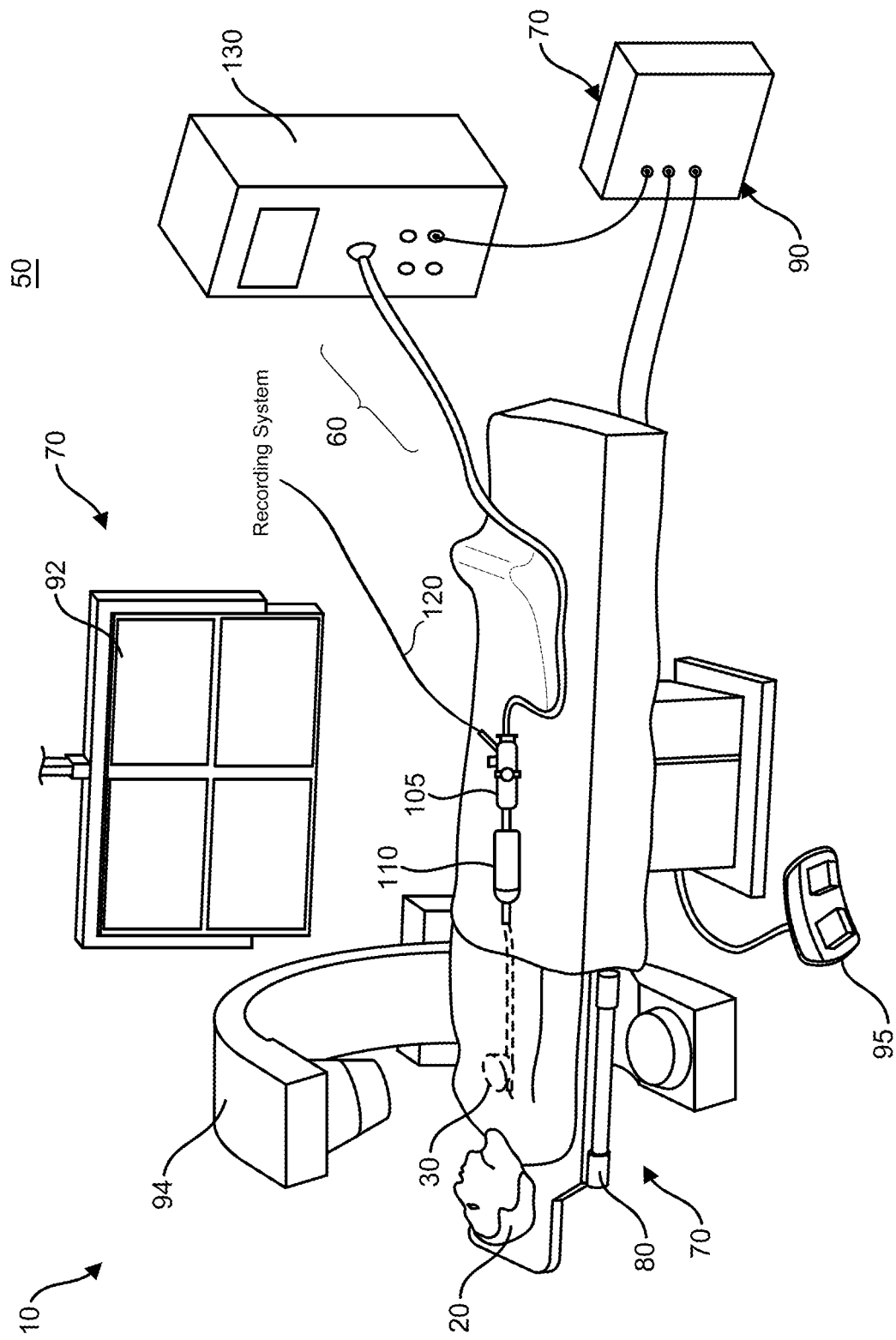
FIG. 1 is a simplified schematic of an exemplary clinical setting for an electrophysiology system including a cryoablation catheter system and an electroanatomical mapping system according to embodiments of the disclosure.

While the embodiments described herein are amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

FIG. 1 is a simplified schematic of an exemplary clinical setting 10 for treating a patient 20, and in particular, a heart 30 of the patient 20, using an electrophysiology system 50 according to various embodiments of the disclosure. In the illustrated embodiment, the electrophysiology system 50 includes a cryoablation catheter system 60, and an electroanatomical mapping (EAM) system 70, which in turn, includes a localization field generator 80, a mapping and navigation controller 90, and a display 92. As further shown, in the exemplary embodiment, the clinical setting 10 further includes additional equipment such as imaging equipment (represented by the C-arm 94) various controller elements, such as a foot controller 95, configured to allow an operator to control the various aspects of the electrophysiology system 50, and, optionally, additional diagnostic and therapeutic components, e.g., an EP recording system such as is known in the art. As will be appreciated by the skilled artisan, the specific arrangement and composition of the clinical setting 10 is not of particular importance to the present disclosure except as described in detail herein.

In the illustrated embodiment, the cryoablation catheter system 60 includes a cryoablation catheter 105, an introducer sheath 110, a mapping catheter 120 and a cryoablation console 130. Additionally, the cryoablation catheter system 60 further includes various components, e.g., connecting elements such as cables, umbilicals, and the like, that operate to functionally connect the various components of the cryoablation catheter system 60 to one another and to the components of the EAM system 70. The particular arrangement of connecting elements is not of critical importance to the present disclosure, and the skilled artisan will recognize that the various components described herein can be interconnected in a variety of ways.

In the various embodiments, the cryoablation catheter system 60 is configured to deliver cryogenic ablative energy to target tissue of the patient's heart 30 to create tissue necrosis, rendering the ablated tissue incapable of conducting electrical signals. In particular, as will be described in greater detail below, the cryoablation catheter 105 includes a therapy delivery element in the form of an inflatable balloon (described and illustrated in detail elsewhere herein) that can be advanced intravascularly to the cardiac chamber of interest and receive cryogenic fluid (e.g., nitrous oxide) and deliver the cryogenic energy to the tissue to be ablated. In particular embodiments, as will be readily recognized by the skilled artisan, the cryoablation catheter 105 can be used to ablate the tissue of the ostia of the pulmonary veins to treat atrial fibrillation. However, the various embodiments described herein are not limited to any particular clinical application or procedure. The cryoablation console 130 is operable to control the various functional aspects of the cryoablation catheter system 60 and to supply the cryogenic fluid to the cryoablation catheter 105.

In embodiments, the introducer sheath 110 is operable to provide a delivery conduit through which the cryoablation catheter 105 can be advanced to the specific target sites within the patient's heart 30. Additionally, the mapping catheter 120 can be advanced in combination with the cryoablation catheter 105, and includes sensing electrodes operable to acquire, among other things, intrinsic electrical activation signals for use by the operator in assessing target tissue sites, ablation effectiveness, and the like. In the illustrated embodiment, the mapping catheter 120 is operatively coupled to an electrophysiology recording system (not shown) configured for displaying processing and diagnostic information acquired by the mapping catheter 120. In other embodiments, the mapping catheter 120 may be operatively coupled to the cryoablation console 130 and/or the EAM system 70.

The EAM system 70 is operable to track the location of the various functional components of the cryoablation catheter system 60, and to generate high-fidelity three-dimensional anatomical and electroanatomical maps of the cardiac chambers of interest. In embodiments, the EAM system 70 can be the RHYTHMIA™ HDx mapping system marketed by Boston Scientific Corporation.

As will be appreciated by the skilled artisan, the particular depiction of the electrophysiology system 50 shown in FIG. 1 is intended to provide a general overview of the various components, and is not in any way intended to imply that the disclosure is limited to any particular arrangement. For example, the skilled artisan will readily recognize that additional hardware components, e.g., breakout boxes, workstations, and the like, will be included in the electrophysiology system 50.

As will be readily understood by the skilled artisan, the EAM system 70 generates a localization field, via the field generator 80, to define a localization volume about the heart 30, and one or more location sensors or sensing elements on the tracked device(s), e.g., the cryoablation catheter 105, the introducer sheath 110 and/or the mapping catheter 120, generate an output that can be processed by the mapping and navigation controller 90 to track the location of the sensor, and consequently, the corresponding device, within the localization volume. In the illustrated embodiment, the device tracking is accomplished using magnetic tracking techniques, whereby the field generator 80 is a magnetic field generator that generates a magnetic field defining the localization volume, and the location sensors on the tracked devices are magnetic field sensors.

In other embodiments, impedance tracking methodologies may be employed to track the locations of the various devices. In such embodiments, the localization field is an electric field generated, for example, by an external field generator arrangement (e.g., surface electrodes positioned on the patient's body), by intra-body or intra-cardiac devices (e.g., an intracardiac catheter), or both. In these embodiments, the location sensing elements can constitute electrodes on the tracked devices that generate outputs received and processed by the mapping and navigation controller 90 to track the location of the various location sensing electrodes within the localization volume.

In embodiments, the EAM system 70 is equipped for both magnetic and impedance tracking capabilities. In such embodiments, impedance tracking accuracy can, in some instances be enhanced by first creating a map of the electric field induced by the electric field generator within the cardiac chamber of interest using a probe equipped with a magnetic location sensor, as is possible using the aforementioned RHYTHMIA HDx™ mapping system. One exemplary probe is the INTELLAMAP ORION™ mapping catheter marketed by Boston Scientific Corporation.

Regardless of the tracking methodology employed, the EAM system 70 utilizes the location information for the various tracked devices, along with cardiac electrical activity acquired by, for example, the mapping catheter 120 or another catheter or probe equipped with sensing electrodes, to generate, and display via the display 92, detailed three-dimensional geometric representations of the cardiac chambers as well as electroanatomical maps in which cardiac electrical activity of interest is superimposed on the geometric representation. Furthermore, the EAM system 70 can also generate a graphical representation of the various tracked devices within the aforementioned geometric or electroanatomical map.

However, current cryoablation catheter systems have heretofore not been integrated with existing EAM systems due, at least in part, to inherent structural limitations of the components of the cryoablation catheter systems. The embodiments of the present disclosure overcome these limitations by integrating the cryoablation catheter system 60 with the EAM system 70 to allow the therapy elements of the cryoablation catheter 105, as well as other components such as portions of the introducer sheath 110 and/or the mapping catheter 120, to be visualized on an electroanatomical map. The integrated system of the present disclosure thus has the capability to enhance the efficiency of clinical workflows and reduce reliance on fluoroscopy for cryoablation catheter visualization. The various embodiments include improved guidance for maneuvering and placement of cryoablation catheter system components without the need for fluoroscopy and for creating anatomic and electroanatomic maps, and display and annotation of information related to the location, state, and therapeutic dose of the cryogenic balloon. In some embodiments, the electrophysiology system 50 provides the capability to generate geometric anatomical maps of the cardiac chamber, e.g., the left atrium, without the need for a separately tracked probe.

Figure 2A:
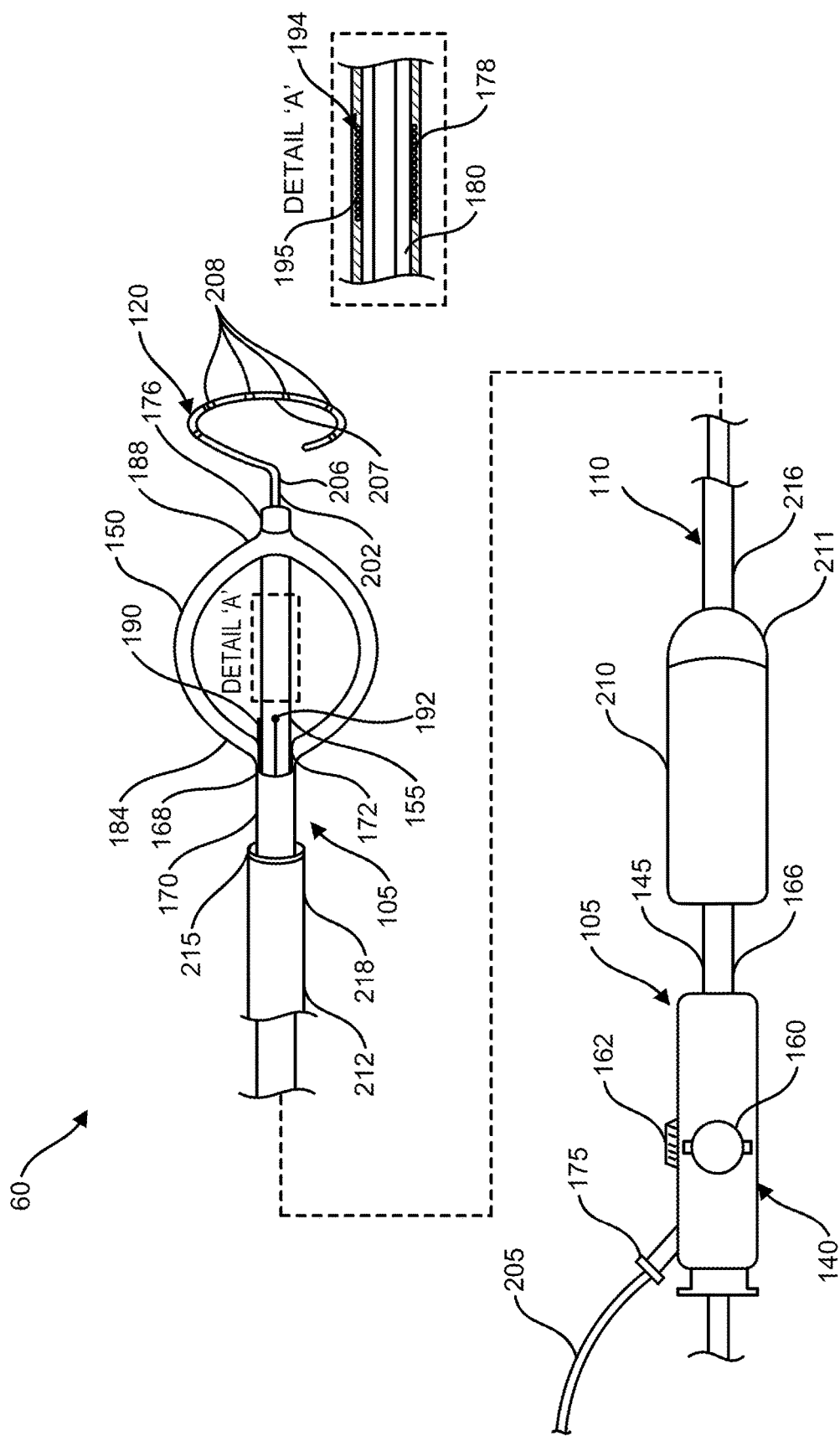
FIGS. 2A-2C are schematic illustrations of a portion of the cryoablation catheter system of FIG. 1 according to embodiments of the disclosure.
Figure 2B:
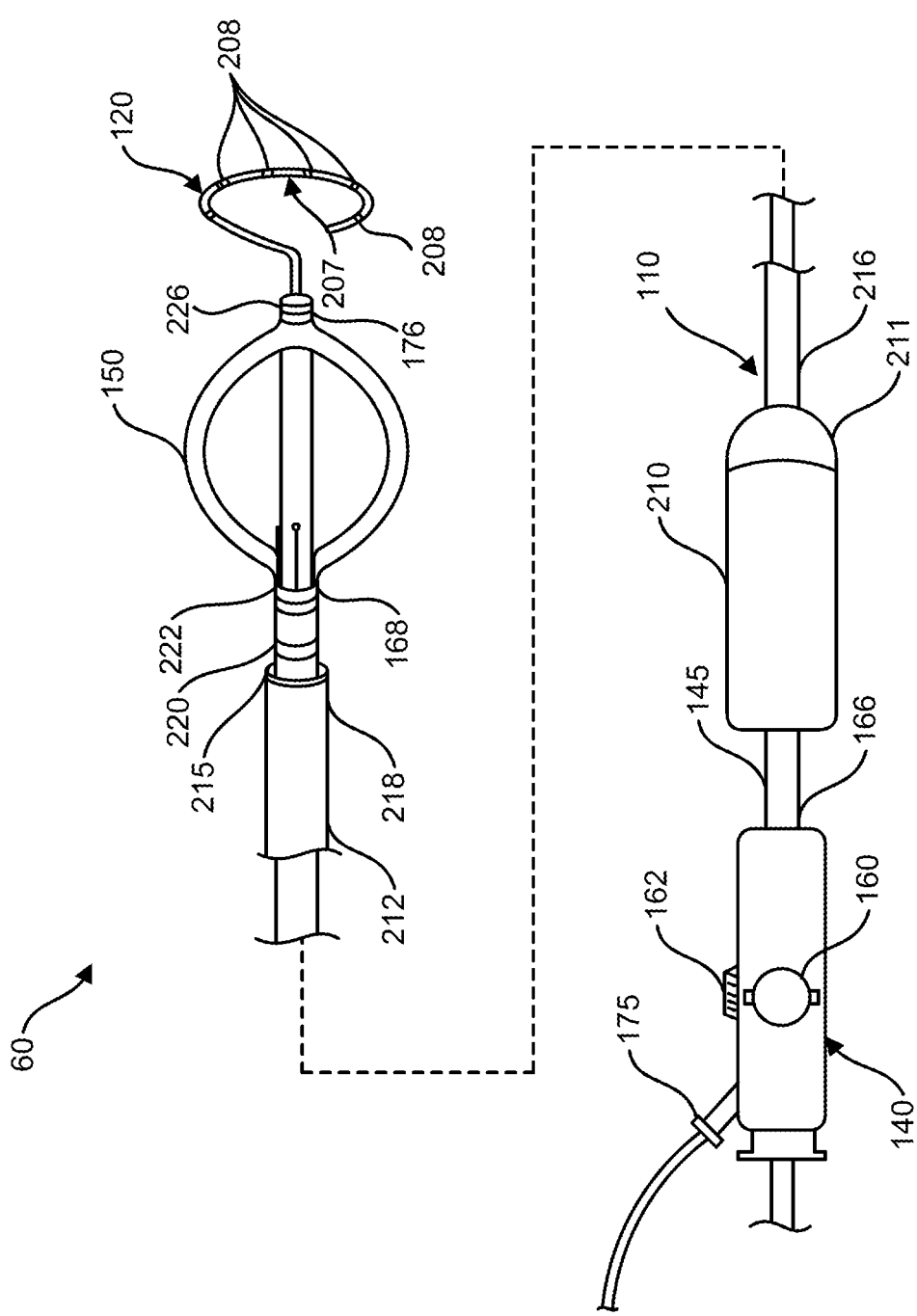
Figure 2C:
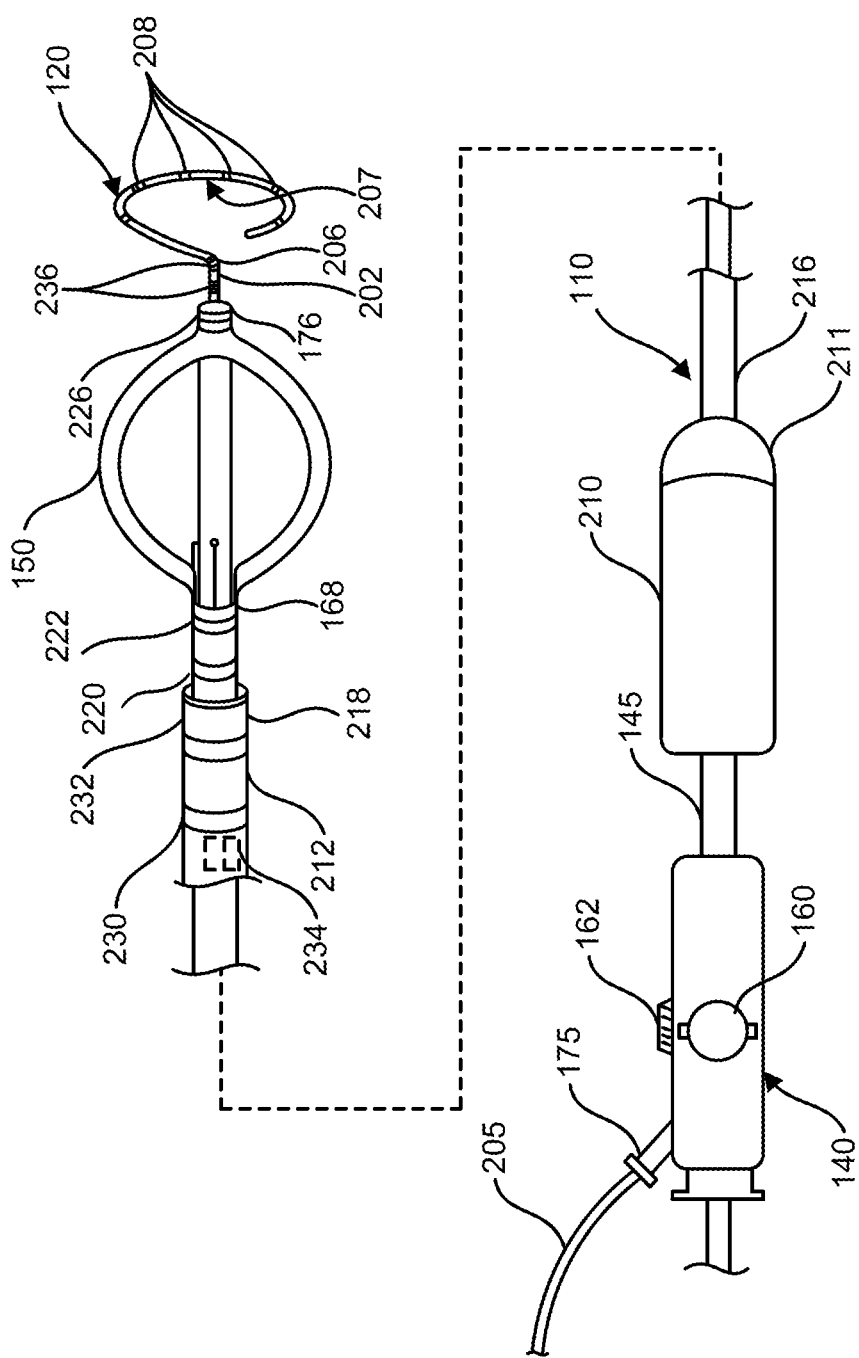

FIGS. 2A-2C are schematic illustrations of a portion of the cryoablation catheter system 60 according to embodiments of the disclosure. With reference to FIGS. 2A-2C collectively, in the illustrated embodiment, the cryoablation catheter 105 includes a handle 140, a tubular shaft 145, a cryoballoon 150 (shown partially cut away in FIG. 2A for illustration purposes) and a guidewire lumen member 155.

As shown, the handle 140 includes various elements including a deflection control member 160 and a slider 162. The cryoablation catheter shaft 145 has a proximal end 166, an opposite distal end 168, and a shaft wall 170 defining a shaft lumen 172. Additionally, the guidewire lumen member 155 has a proximal end 175, an opposite distal end 176, and a guidewire lumen member wall 178 extending therebetween and defining a guidewire lumen 180. As further shown, the cryoballoon 150 (shown in an expanded, inflated state in FIGS. 2A-2C) has a proximal portion 184 and an opposite distal portion 188.

The proximal end of the cryoablation catheter shaft 145 is coupled to and extends distally of a distal end of the cryoablation catheter handle 140. In embodiments, the deflection control member 160 is operable by the user to deflect the distal region of the cryoablation catheter shaft 145, as is known in the art. The particular deflection mechanism used for control of the distal region of the shaft 145 is not critical to the present disclosure, and as such, any catheter deflection/steering technology, whether now known or later developed, can be used within the scope of the present disclosure.

As further shown, the proximal portion 184 of the cryoballoon 150 is attached to the distal end 168 of the cryoablation catheter shaft 145, and the distal portion 188 of the cryoballoon 150 is attached to the distal end 178 of the guidewire lumen member 155. The cryoballoon 150 is capable of transitioning between a deflated, unexpanded state (not shown) and the inflated, expanded state illustrated in FIGS. 2A-2C. In embodiments, the cryoballoon 150 can be constructed according to any means in the art, whether now known or later developed, suitable for cryoablation catheter balloons. In embodiments, the cryoballoon design and construction can be any of those described in commonly assigned International Application Nos. PCT/US18/032580 and PCT/US18/40908, which are incorporated herein by reference in their entireties.

The guidewire lumen member 155 is tubular and extends within the cryoablation shaft lumen 172. In embodiments, the guidewire lumen member 155 is configured to be slidable within the cryoablation shaft lumen 172 to accommodate changes in the axial length of the cryoballoon 150 as it transitions between its deflated and inflated states. In embodiments, the guidewire lumen member 155 is coupled to the slider 162, such that the operator can control the axial translation of the guidewire lumen member 155. This can be particularly advantageous during deflation of the cryoballoon 150 to control the shape of the cryoballoon 150 and avoid bunching, etc.

In various embodiments, the cryoablation catheter 105 is equipped with additional sensing components to provide information regarding the operation of the cryoablation catheter system 60 for use in its control. As shown in FIGS. 2A-2C, for example, the cryoablation catheter 105 includes a pressure sensor element 190 and a temperature sensor element 192 disposed within the interior space defined by the cryoballoon 150 to provide information to the cryoablation console 130 and/or the EAM system 70 as well as the operator. In the illustrated embodiment, the pressure sensor element 190 comprises a small-diameter tube that is open to the interior space within the cryoballoon 150 so as to be capable of transmitting the hydrostatic fluid pressure within the cryoballoon 150 to a pressure sensor (not shown) located elsewhere, e.g., within the handle 140. Further, the temperature sensor element 192 as shown is a thermocouple, thermistor, or the like, disposed on the guidewire lumen member 155 within the interior of the cryoballoon 150. The particular representation of the pressure sensor element 190 and the temperature sensor element 192 shown in FIG. 2A is exemplary only, and any of a number of configurations for accomplishing the associated pressure and temperature sensing functionality of these components can be used within the scope of the disclosure. For example, in embodiments, the pressure sensor element 190 may comprise a pressure sensor disposed within the interior volume of the cryoballoon 150.

Additionally, as can be further seen in FIG. 2A, the cryoablation catheter 105 further includes a location sensor 194 disposed on the guidewire lumen member 155. In the illustrated embodiment, as shown in the partial cross-sectional view labeled "Detail A" in FIG. 2A, the location sensor 194 is formed of a plurality of turns of conductive wire 195 defining an inductive magnetic sensor coil, with the turns of conductive wire 195 being embedded in the guidewire lumen member wall 178. The illustrated configuration thus defines an air-core inductive magnetic sensor with the conductive wire 195 being disposed circumferentially around the guidewire lumen 180. This configuration advantageously maintains the patency of the guidewire lumen 180 to accommodate the passage of additional probes or devices, such as the mapping catheter 120.

In alternative embodiments, the conductive wire 195 could be embedded within the cryoablation catheter shaft wall 170 at a location proximal to the cryoballoon 150.

In other embodiments, the inductive magnetic location sensor 194 can be located within the guidewire lumen 180 itself.

Although the embodiment of FIG. 2A illustrates an inductive magnetic location sensor 194, in other embodiments, other types of magnetic location sensors can be employed. Exemplary location sensors include magneto-resistive (MR) sensors, Hall-effect sensors, and the like. Additionally, in embodiments, particularly those employing MR sensors, multiple location sensor 194 can be positioned at different locations on the guidewire lumen member 155 or the cryoablation catheter shaft 145, which can advantageously provide expanded degrees of freedom as compared to the embodiment specifically illustrated in FIG. 2A.

As further shown in FIGS. 2A-2C, the mapping catheter 120 includes a shaft 202 having a proximal portion 205, an opposite distal portion 206, and a mapping portion 207 extending distally of the shaft distal portion 206 and including a plurality of mapping or sensing electrodes 208. In embodiments, the mapping catheter 120 is configured to be disposed within the guidewire lumen 180, and is dimensioned such that the mapping catheter proximal portion 205 extends proximally from the guidewire lumen member proximal end 175 with the mapping portion 207 extending distally of the guidewire lumen member distal end 176. The mapping portion 207 has a pre-formed circular or semi-circular shape when unconstrained by the guidewire lumen member 155. Mapping catheters 120 of the type shown in FIGS. 2A-2C are generally known, and as such, the particular construction of the mapping catheter 120 is not critical to the present disclosure.

As further shown, the introducer sheath 110 has a sheath handle 210 including a control knob 211, and an elongate, tubular sheath wall 212 defining a sheath lumen 215 and having a proximal end 216 and an opposite distal end 218. Generally speaking, the introducer sheath 110 has a deflectable or steerable distal portion, as is known in the art, with the deflection being controllable by the operator using the control knob 211. However, the particular construction or type of introducer sheath 110 is not of critical importance to the present disclosure except as to the extent described herein. As shown in FIGS. 2A-2C, the introducer sheath 110 is configured such that the cryoablation catheter shaft 145, and consequently the cryoballoon 150, can be slidably and rotatably disposed through the sheath lumen 215, as is known in the art.

The location sensor 194 is configured to generate a cryoablation location signal when in the location sensor 194 is within a magnetic localization field generated by the magnetic field generator 80 (see FIG. 1) to provide for localization of the cryoballoon 150 within the anatomical chamber of interest. This in turn allows for direct tracking of the position of the cryoballoon 150 and the ability to incorporate a graphical representation of the cryoballoon 150 on an anatomical or electroanatomical map created by the EAM system 70.

Additionally, the presence of the sensing electrodes 208 on the mapping portion 207 of the mapping catheter 120 allows the mapping portion 207 to be tracked using impedance tracking techniques as described elsewhere, and to be incorporated in an anatomical or electroanatomical map along with the cryoballoon 150. As such, FIG. 2B illustrates an alternative embodiment of the cryoablation catheter system 60 that is substantially identical to the embodiment of FIG. 2A, but wherein the cryoablation catheter 105 includes current injection electrodes 220, 222 axially spaced along the cryoablation catheter shaft 145, and a distal current injection electrode 226 disposed at the guidewire lumen member distal end 176. In embodiments, the electrodes 220, 222 and 226 are operatively coupled to an electric current source (e.g., within the mapping and navigation controller 90, see FIG. 1) so as to be capable of generating a local electric field proximate the distal end region of the cryoablation catheter 105. Because the locations of the current injection electrodes 220, 222 and 226 relative to the location sensor 194 are known, the local electric field can be used to more precisely track the locations of the sensing electrodes 208 using impedance tracking techniques than could be accomplished relying solely on an externally-generated electric field.

FIG. 2C illustrates yet another alternative embodiment of the cryoablation catheter system 60 that is substantially identical to the embodiment of FIG. 2B. However, in the embodiment of FIG. 2C, the introducer sheath 110 is equipped with sheath electrodes 230, 232 and/or a sheath location sensor 234 disposed near the distal end 218 of the introducer sheath 110. Additionally, the mapping catheter 120 includes mapping catheter shaft electrodes 236 disposed on the mapping catheter shaft 202 in the distal portion 206 just proximal to the mapping portion 207. The additional electrodes 230, 232 and/or sensor 234 operate to further enhance the tracking capabilities of the EAM system 70. For example, the sheath electrodes 230, 232 can be operable as current injection electrodes in addition to, or in lieu of, the cryoablation catheter current injection electrodes 220, 222 and 226 for use in local impedance tracking of the sensing electrodes 208 of the mapping catheter 120, particularly when the sheath location sensor 234 (which can be in the form of an inductive sensor, MR sensor, or the like) is also present for directly magnetically tracking the location of the sheath distal end 218. Alternatively, or additionally, the sheath electrodes 230, 232 can be operable to allow for direct impedance tracking of the sheath distal end 218.

Similarly, the mapping catheter shaft electrodes 236 can also facilitate direct impedance tracking of the mapping catheter 120 more accurately than can be accomplished solely with the sensing electrodes 208.

Figure 3:
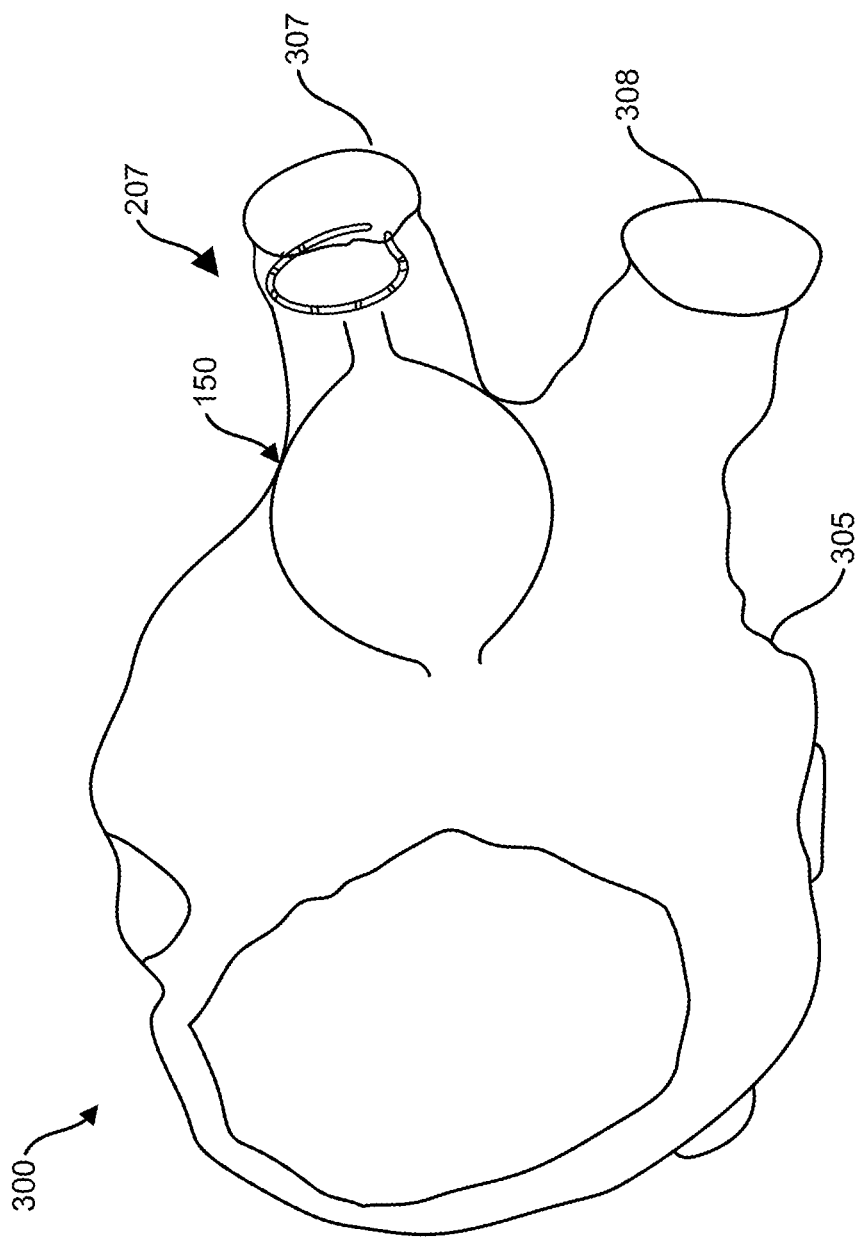
FIG. 3 is an illustration of an exemplary anatomical map of a patient's left atrium showing the distal end portion of the cryoablation catheter of FIG. 1, according to embodiments of the disclosure.

FIG. 3 illustrates an exemplary schematic outline of a geometrical anatomical map 300 of a patient's left atrium 305 as could be generated by the electrophysiology system 50 of FIG. 1. For illustration purposes, the anatomical map 300 is shown in outline form only, although the skilled artisan will readily recognize that in practice, the anatomical map 300 may include texturing, annotations, etc. to provide the clinician with enhanced visualization of the chamber geometry.

As shown in FIG. 3, renderings of both the cryoballoon 150 and the mapping portion 207 of the mapping catheter 120 can be displayed in the anatomical map 300 to localize the cryoballoon 150 and/or the mapping portion relative to anatomical features of interest, e.g., the pulmonary veins 307, 308. In embodiments, additional components of the electrophysiology system 50 can also be rendered on the anatomical map 300. For example, with reference to the embodiment of FIG. 2C, the inclusion of the sheath electrodes 230, 232 may facilitate localization of the introducer sheath distal end 218, whether by direct impedance tracking of the sheath electrodes 230, 232, or by local impedance tracking of these electrodes using the electrodes 220, 222 of the cryoablation catheter 105 as current injecting electrodes in the same manner as described in connection with local impedance tracking of the sensing electrodes 208 on the mapping catheter 120.

Additionally, or alternatively, the in embodiments, the distal portion 206 of the mapping catheter shaft 202 can be impedance tracked using the mapping catheter shaft electrodes 236 and then displayed in conjunction with the anatomical map 300.

In embodiments, additional functional components can be included in, or used in conjunction with, the illustrated components of the cryoablation catheter system 60. For example, in embodiments (not shown), a guidewire or comparable device could extend through the guidewire lumen 180 distally beyond the cryoballoon 150 to facilitate advancement of the cryoballoon 150 to the target site. In such embodiments, the guidewire can be electrically connected to the EAM system 70, which can thereby impedance or magnetically (if the guidewire is equipped with a magnetic tracking or location sensor) track the tip of the guidewire and render it on the display 92 along with the cryoballoon 150 and/or the deliver sheath distal end 218.

In embodiments, the electrophysiology system 50 is capable of determining the operating state of the cryoballoon 150, e.g., its state of inflation, inflated geometry (e.g., diameter and length), internal temperature, and the like, and of rendering the graphical representation of the cryoballoon 150 in such a way as to represent the desired operating condition(s). For example, the mapping and navigation controller 90 can receive the output from the pressure sensor element 190 and based on this and stored mechanical properties of the cryoballoon 150, e.g., inflated diameter vs. pressure, compliance, etc. render a depiction of the cryoballoon 150 that accurately represents its inflation state.

In another non-limiting example, the internal cryoballoon 150 temperature, as measured by the temperature sensor element 192, can be depicted by color-coding the depiction of the cryoballoon 150 on the anatomical map 300. In embodiments, additional graphical indicators of cryoballoon 150 operating conditions, e.g., temperature, pressure, inflation percent, and the like, can be presented to the operator on the display 92.

In other embodiments, the cryoballoon 150 operating state is based on a control input to or from the cryoablation console 60 (e.g., that the system is in or has completed an inflation phase, a treatment phase, or a thaw phase) in lieu of, or in addition to the use of pressure and/or temperature sensor signals.

In some embodiments, the navigation-enabled cryoablation catheter 105 can be used to create detailed anatomical maps without the need for a separate mapping procedure independent of the cryoablation procedure. For example, the distal portion of the cryoablation catheter 105 can be maneuvered around the cardiac chamber, e.g., the left atrium 305, with the cryoballoon 150 in a deflated, partially inflated, or fully inflated state, to create an anatomical map such as the anatomical map 300. In particular embodiments, the capability to determine the inflated geometry of the cryoballoon 150 facilitates rapid generation of the anatomical maps of the cardiac chamber of interest. That is, the capability to accurately determine the inflated geometry of the cryoballoon 150, coupled with the known spatial relationship between the wall of the cryoballoon 150 and the location sensor 194, facilitates rapid mapping of the geometry of the cardiac chamber as the inflated cryoballoon 150 is swept within the chamber due in part to the relatively large volume assumed by the cryoballoon 150 when inflated (as compared to conventional, navigation-enabled linear catheters).

Additionally, the resolution of the anatomical map 300 can, in some cases, be further enhanced by the EAM system 70. For example, geometric features and landmarks of an initial anatomical map 300 can be used by the mapping and navigation controller 90 as a guide to register or align a three-dimensional image obtained through an imaging modality (e.g., CT, MRI, 3D ultrasound) that is imported into the mapping and navigation controller 90, which in turn matches those features to corresponding features on the anatomical map 300 and transforms the position of the associated CT/MRI image until it optimally aligns with the anatomical map 300. The imported CT or MRI image may provide a superior representation of the patient's cardiac anatomy and therefore provide improved guidance for maneuvering and placement of the cryoablation catheter 105 therein.

In embodiments, the mapping portion 207 of the mapping catheter 120 can be operable to further enhance the functionality available to the operator from the cryoablation catheter system 60. For example, local impedance measurements from sensing electrodes 208 can be used to sense contact with tissue and further enhance the feedback to the operator in, among other things, navigating the cryoablation catheter 105 and the mapping catheter 120 within the chamber of interest, creating anatomical the map 300, and alerting the operator to the proximity of the guidewire lumen member distal end 176 to tissue to manage perforation risk.

In various embodiments (not shown), the cryoablation catheter 105 may be equipped with electrodes on the cryoballoon 150 to allow for direct impedance tracking of the cryoballoon 150. In exemplary embodiments, the cryoablation catheter 105 can be configured in the same or similar manner as any of the cryoablation catheters disclosed in commonly assigned International Application No. PCT/US18/16026, which is incorporated herein by reference. In addition to facilitating direct impedance tracking, the presence of electrodes on the cryoballoon 150 can facilitate localized assessment of tissue contact along different portions of the cryoballoon 150, assessment of pulmonary vein occlusion, and the like.

FIGS. 4A-4D are schematic illustrations of a portion an alternative cryoablation catheter system 400 according to additional embodiments of the disclosure. In many respects the features of the cryoablation catheter system 400 are similar or substantially identical to corresponding features of the cryoablation catheter system 60. As such, the cryoablation catheter system 400 includes a cryoablation catheter 405, in introducer sheath 410 and a mapping catheter 420. The cryoablation catheter 405 further includes a handle 440, a tubular shaft 445, a cryoballoon 450 and a guidewire lumen member 455. Additionally, cryoablation catheter shaft 445 includes a distal end 468 and a shaft lumen (not visible in FIGS. 4A-4D, but see FIGS. 2A-2C for an equivalent structure), and the guidewire lumen member 455 has a proximal end 475, a distal end 476 and a guidewire lumen 480, and is slidable within the shaft lumen. As with the cryoablation catheter 105, the cryoballoon 450 has a proximal portion 484 attached to the distal end of the shaft 445, and a distal portion 488 attached to the guidewire lumen member distal end 476.

As further shown in FIGS. 4A-4D, the mapping catheter 420 includes a shaft 502 having a proximal portion 505, an opposite distal portion 506, and a mapping portion 507 extending distally of the shaft distal portion 506 and including a plurality of mapping or sensing electrodes 508. In embodiments, the mapping catheter 420 is configured to be disposed within the guidewire lumen 480, and is dimensioned such that the mapping catheter proximal portion 505 extends proximally from the guidewire lumen member proximal end 475 with the mapping portion 507 extending distally of the guidewire lumen member distal end 476.

As further shown, the introducer sheath 410 has a sheath handle 510, and an elongate, tubular sheath wall 512 defining a sheath lumen 515 and having a proximal end 516 and an opposite distal end 518.

Unlike the cryoablation catheter 105, the cryoablation catheter 405 lacks a location sensor or location sensing elements such as electrodes for impedance tracking. Rather, in the embodiments of FIGS. 4A-4D, location sensing elements are disposed on one or both of the introducer sheath 410 and the mapping catheter 420, which operate as auxiliary devices that enable estimating or indirectly tracking the cryoballoon 450 so that it can be incorporated into an anatomical map generated by the EAM system 70.

With reference to the embodiment of FIG. 4A, the mapping catheter 420 includes a mapping catheter location sensor 550 disposed at the shaft distal portion 506 proximal to the mapping portion 507. In embodiments, the location sensor 550 may be an inductive or magneto-resistive magnetic field sensor such as is known in the art, such that the location of the location sensor 550 can be ascertained via magnetic tracking as described elsewhere herein.

Figure 4B:
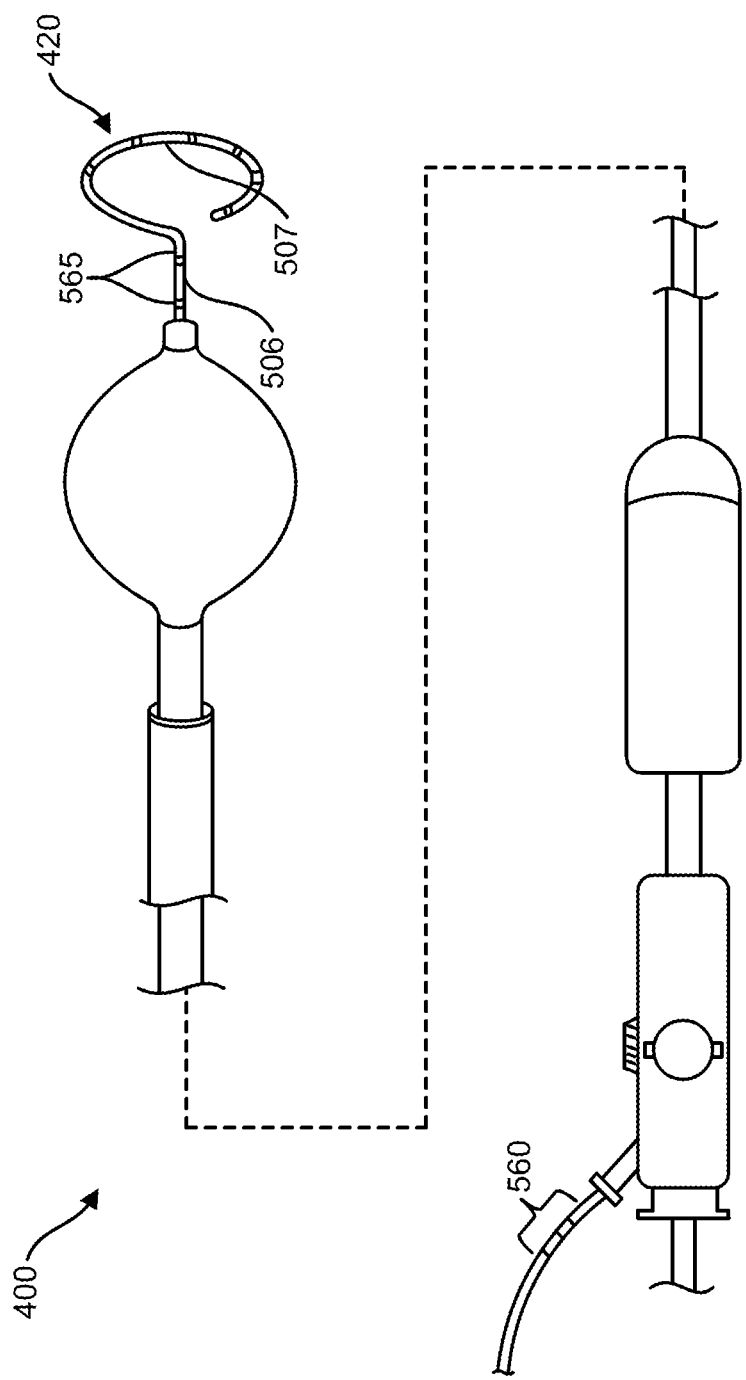
Figure 4C:
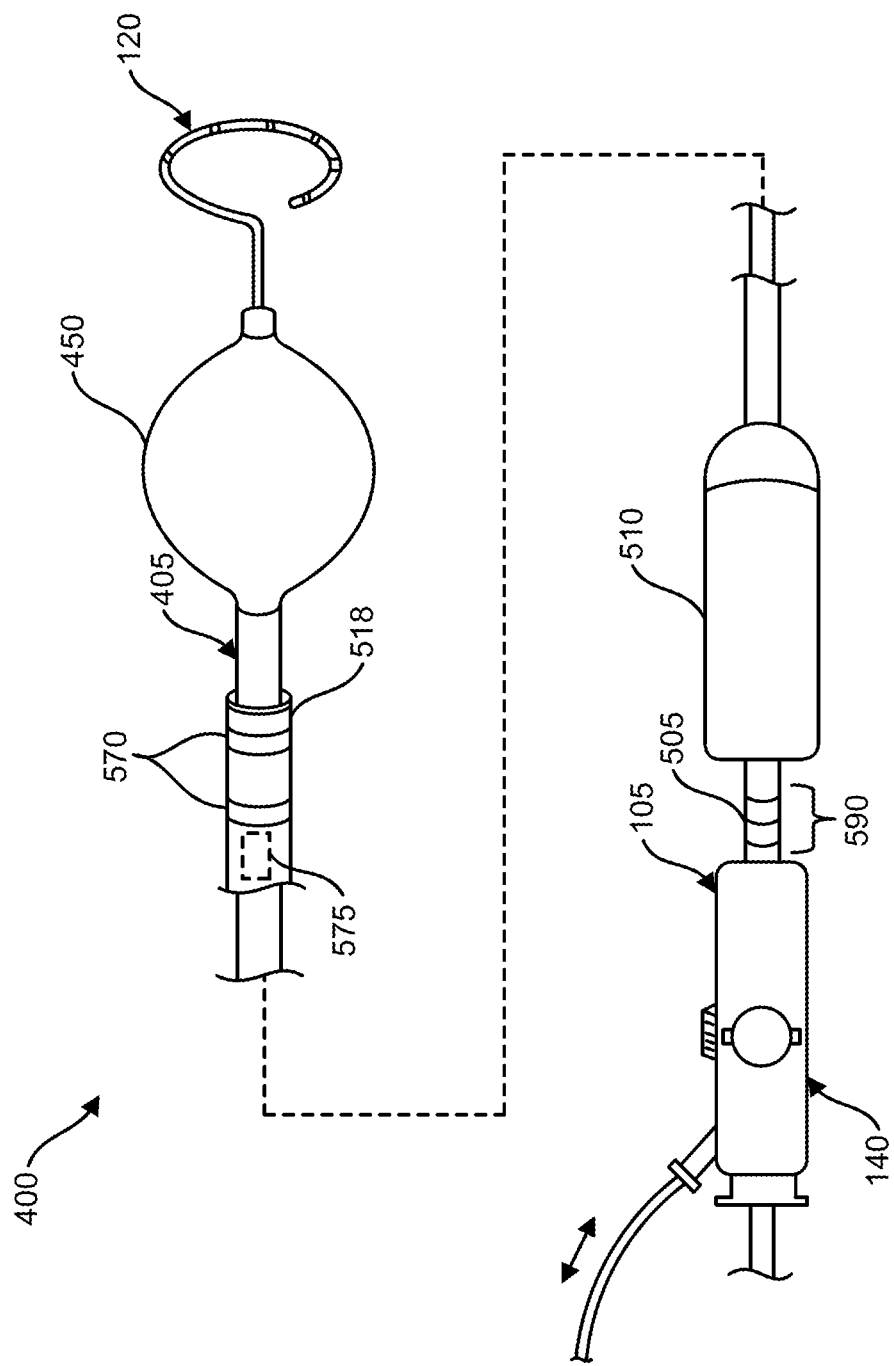

The mapping catheter 420 further includes a relative position indicator to provide an indication of the relative axial position of the location sensor 550 and the cryoballoon 450 when the mapping catheter 420 is disposed within the guidewire lumen 480 as shown in FIGS. 4A-4C. In the embodiment of FIG. 4A, the relative position indicator is in the form of fiducial markers 560 on the proximal portion 505 of the mapping catheter shaft 502. As shown, the fiducial markers 560 can be visualized by the operator.

In embodiments, the presence of the fiducial markers 560 provides the operator with a visual indication of the relative location of each fiducial marker 560 and a selected landmark on the cryoablation catheter 405 (e.g., the proximal end of the guidewire lumen member 475). The fiducial markers 560 are located at pre-selected positions on the mapping catheter shaft 502 such that the position of the fiducial markers 560 relative to this selected landmark on the cryoablation catheter 405 provides an estimate of the relative position of, for example, the axial center of the cryoballoon 450 and the location sensor 550. This allows the EAM system 70 to estimate the position of the cryoballoon 450 and, in response to an operator input, generate a graphical representation of this estimated cryoballoon 450 position on an anatomical map.

The embodiment of FIG. 4A thus provides the means to provide at least an estimated location of the cryoballoon 450 on the anatomical map without requiring location sensors or other localization elements on the cryoablation catheter 405 itself.

The embodiment of the cryoablation catheter system 400 illustrated in FIG. 4B is substantially the same as that of FIG. 4A, with the exception that in the embodiment of FIG. 4B, the mapping catheter 420 includes a plurality of electrodes 565 on the mapping catheter shaft distal portion 506 in lieu of the location sensor 550. The electrodes 565 facilitate localization of the mapping catheter distal portion 506 using impedance tracking rather than magnetic tracking.

The embodiment of FIG. 4C differs from that of FIGS. 4A and 4B in that in the cryoablation catheter system 400 of FIG. 4C, the introducer sheath 410, and not the mapping catheter 420, are equipped with location sensing elements. That is, as shown in FIG. 4C, the introducer sheath 410 includes sheath electrodes (e.g., ring electrodes) 570 and/or a sheath location sensor 575 located proximate the sheath distal end 518, for use in tracking the location of the sheath distal end 518 via impedance tracking or magnetic tracking, respectively. Additionally, the cryoablation shaft proximal portion 505 includes relative position indicators in the form of fiducial markers 590 that are user-accessible and provide the operator with a visual indication of the relative location of each fiducial marker 590 and a selected landmark on the introducer sheath handle 510. In this way, the position of the cryoballoon 450 within the anatomical chamber can be estimated and rendered in much the same manner as described above with respect to the embodiment of FIG. 4B.

Figure 4D:
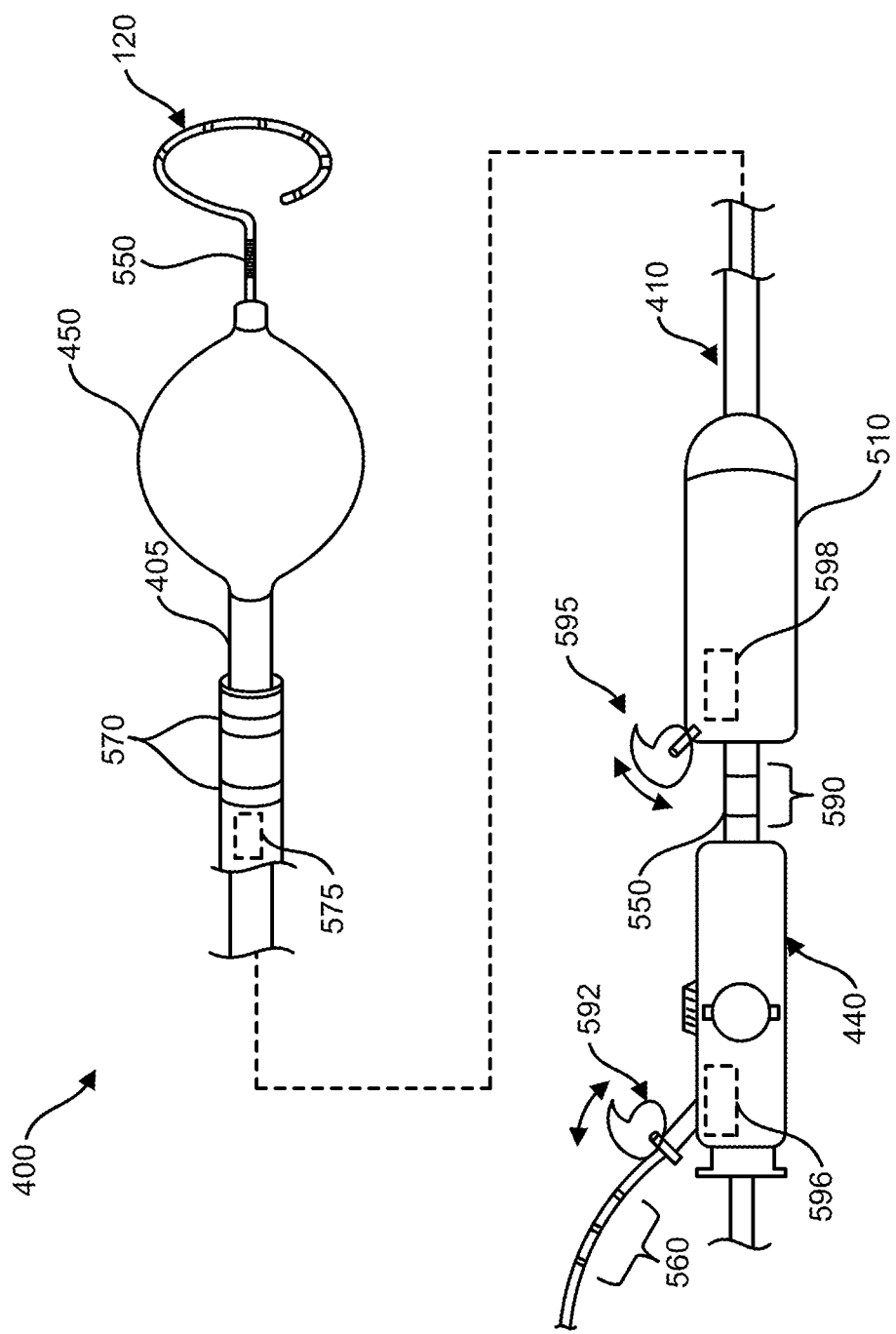

FIG. 4D illustrates yet another alternative embodiment of the cryoablation catheter system 400. The embodiment of FIG. 4D includes the mapping catheter location sensor 550 and the mapping catheter fiducial markers 560 (see FIG. 4A), as well as the sheath electrodes 570, sheath location sensor 575, and fiducial markers 590 on the cryoablation shaft proximal portion 505. The embodiment of FIG. 4D further includes locking elements 592, 595 positioned, respectively, on the mapping catheter 405 and the introducer sheath 410. The locking element 592 is configured to allow the operator to selectively lock the relative positions of the mapping catheter 420 and the cryoablation catheter 405. Similarly, the locking element 595 is configured for selectively locking the relative positions of the cryoablation catheter 405 and the introducer sheath 410. The inclusion of the locking elements 592, 595 and the ability to lock the relative positions of the corresponding components further enhances the accuracy of the rendered location of the cryoballoon 450 by inhibiting unintended relative movement of the cryoablation catheter 405 and the auxiliary device that is being directly tracked by the EAM system 70. In the illustrated embodiment, the locking elements 592, 595 are depicted as simple mechanical clamps, but this is not intended to be in any way limiting. That is, any means for mechanically securing the positions of the respective components relative to one another without placing undue stress thereon may be used. In various embodiments, swaged fittings, snap-fit connections, and the liked may be used.

As further shown, the embodiment of FIG. 4D, the cryoablation catheter handle 440 further includes a fiducial sensor 596, and the sheath handle 510 includes a fiducial sensor 598. The fiducial sensors 596, 598 are configured to automatically detect the positions of, respectively, the fiducial markers 560 and 590. In embodiments, the fiducial sensors may be optical sensors, mechanical sensors, electromechanical sensors, and the like. In short, any component capable of automatically detecting the position of the fiducial markers 560, 590. The inclusion of the fiducial sensors 596, 598 facilitates automatic indirect tracking of the position of the cryoballoon 450 based on the directly tracked position of the location elements on the mapping catheter 420 and/or the introducer sheath 410.

In the embodiments of FIG. 4A-4D, the relative position indicators in the form of the fiducial markers provide visual indications of the relative positions of the mapping catheter 420 or the introducer sheath 410 and the cryoablation catheter 405. In other embodiments, other relative position indicators can be employed. In exemplary embodiments, the relative position indicator can be configured to provide tactile feedback to a user indicative of the relative position of the cryoballoon and the location sensing element on the respective auxiliary device.

Although in the illustrated embodiments the auxiliary devices comprise one or both of the introducer sheath 410 and the mapping catheter 420, the disclosure is not limited to such devices. For example, in embodiments, the auxiliary device could take the form of a dilator (e.g., for use in transseptal crossing procedure to access the left atrium) or similar stylus. In embodiments, the auxiliary device could be a guidewire or stylet used for advancing the disclosed cryoablation catheters or introducer sheaths to the target anatomical locations. Still other types of probes and devices that could operate as auxiliary devices within the present disclosure will be apparent to those skilled in the art based.

Additional variations of the embodiments of the disclosure, and corresponding functionality, will be readily apparent to the skilled artisan based on the foregoing disclosure. For example, addition of the shaft electrodes 565 in the mapping catheter 420 of FIG. 4D at known locations relative to the mapping catheter location sensor 550 enables local impedance tracking of the sensing electrodes 508, with the shaft electrodes 565 operable as current-injecting electrodes for generating the local electric field, in a similar manner as described above in connection with FIG. 2C.

Additionally, the inclusion of the location sensors 550, 575 on the mapping catheter 420 and the introducer sheath 410 enable one or both of these devices (separately or in combination) to be used to create an anatomical map of a chamber of interest, in the same manner as the cryoablation catheter 105 as described above. In embodiments, inclusion of the electrodes 570 in addition to the location sensor 575 on the introducer sheath 410 enables the generation of electroanatomical maps using the introducer sheath 410 without requiring a dedicated mapping catheter. Similarly, the capability to accurately track the positions of the sensing electrodes 508 of the mapping catheter 420 facilitates creation of electroanatomic maps, as well as electric field maps that can be used in turn to impedance track other devices (such as the cryoablation catheter 105 when equipped with sensing electrodes). As will be appreciated, the forgoing capabilities may enhance clinical efficiency, e.g., by enabling the clinician to generate the electroanatomical maps and tracking electric field maps using the same devices (i.e., the introducer sheath 410 and/or the mapping catheter 420) used in the cryoablation procedure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A cryoablation catheter system comprising:
 a cryoablation catheter comprising:
  a handle,
  a tubular shaft having a shaft proximal end and an opposite shaft distal end, the shaft being defined by a tubular shaft wall forming a shaft lumen extending between the shaft proximal end and the shaft distal end, the shaft proximal end being coupled to and extending distally from the handle, a sheath location sensing element disposed on the shaft distal end, then sheath location sensing element configured to provide a sheath sensor output indicative of a distal shaft end location of the sheath location sensing element within a localization volume response to a localization field, a tubular guidewire lumen member extending within the shaft lumen and having a guidewire lumen member proximal end and an opposite guidewire lumen member distal end disposed distally of the shaft distal end, the guidewire lumen member being defined by a tubular guidewire lumen member wall forming a guidewire lumen extending between the guidewire lumen member proximal end and the guidewire lumen member distal end;

an expandable cryoballoon having a cryoballoon proximal portion attached to the shaft distal end and a cryoballoon distal portion attached to the guidewire lumen member distal end;

an auxiliary device configured for use in combination with the cryoablation catheter, the auxiliary device having a device proximal portion proximate the handle and a device distal portion disposed distal to the cryoballoon, the device distal portion including a device location sensor configured to provide a device sensor output indicative of a device location of the device location sensor within the localization volume responsive to the localization field; and a user-accessible relative position indicator on the handle of the cryoablation catheter and the device proximal portion of the auxiliary device configured to provide an indication of a relative position of the cryoballoon with respect to the sheath location sensing element and the device location sensor within the localization field, the indication of the relative position applicable to the sensed distal shaft end location and the device location to determine an actual location of the cryoballoon.

2. The cryoablation catheter system of claim 1, wherein the relative position indicator includes fiducial markers on the cryoballoon catheter and the auxiliary device.

3. The cryoablation catheter system of claim 2, wherein the fiducial markers are visible to a user.

4. The cryoablation catheter system of claim 2, wherein the cryoablation catheter further comprises a fiducial sensor configured to sense and provide an output indicative of a position of the one or more fiducial markers relative to the fiducial position sensor.

5. The cryoablation catheter system of claim 4, wherein the fiducial sensor is positioned within the handle of the cryoablation catheter.

6. The cryoablation catheter system of claim 5, wherein the fiducial sensor is an optical sensor or an electromechanical sensor.

7. The cryoablation catheter system of claim 1, further comprising a locking element on one or both of the cryoablation catheter and the auxiliary device configured to selectively fix a position of the cryoballoon catheter relative to the auxiliary device.

8. The cryoablation catheter system of claim 7, wherein the locking element is a mechanical locking element configured to secure the cryoablation catheter and the auxiliary device in a fixed position relative to one another.

9. The cryoablation catheter system of claim 1, wherein the auxiliary device is a mapping catheter slidably disposed within the guidewire lumen, the mapping catheter including a mapping catheter distal end portion extending distally of the guidewire lumen member distal end and having a plurality of sensing electrodes.

10. The cryoablation catheter system of claim 1, wherein one or both of the sheath location sensing element and the device location sensor is an electrode and the localization field is an electric field, and wherein the one or both of the sheath sensor output and the device sensor output is a voltage sensed by the electrode when disposed within the electric field.

11. The cryoablation catheter system of claim 1, wherein one or both of the sheath location sensing element and the device location sensor is a magnetic field sensor and the localization field is a magnetic field generated by a field generator of a navigation subsystem.

12. An electrophysiology system comprising:
a cryoablation catheter comprising:
a handle,
a tubular shaft having a shaft proximal end and an opposite shaft distal end, the shaft being defined by a tubular shaft wall forming a shaft lumen extending between the shaft proximal end and the shaft distal end, the shaft proximal end being coupled to and extending distally from the handle,
a sheath location sensing element disposed on the shaft distal end, the sheath location sensing element configured to provide a sheath sensor output indicative of a distal shaft end location of the sheath location sensor within a localization volume response to a localization field,
a tubular guidewire lumen member extending within the shaft lumen and having a guidewire lumen member proximal end and an opposite guidewire lumen member distal end disposed distally of the shaft distal end, the guidewire lumen member being defined by a tubular guidewire lumen member wall forming a guidewire lumen extending between the guidewire lumen member proximal end and the guidewire lumen member distal end;
an expandable cryoballoon having a cryoballoon proximal portion attached to the shaft distal end and a cryoballoon distal portion attached to the guidewire lumen member distal end;
an auxiliary device configured for use in combination with the cryoablation catheter, the auxiliary device having a device proximal portion proximate the handle and a device distal portion positioned distal to the cryoballoon, the device distal portion including a device location sensor configured to provide a device sensor output indicative of a sensed device location of the device location sensor within the localization volume responsive to the localization field;
a user-accessible relative position indicator on the device proximal portion of the auxiliary device configured to provide an indication of a relative position of the cryoballoon with respect to the sheath location sensing element and the device location sensor within the localization field; and
an electroanatomical mapping system comprising:
a localization field generator configured to generate the localization field; and
a navigation and mapping controller configured to determine the sensed location of the sheath location sensing element and the device location sensor within the localization field and to generate a graphical representation of the cryoballoon superimposed on a three-dimensional rendering of an anatomical chamber when positioned therein;

wherein the indication of the relative position applicable to the sensed distal shaft end location and the device location determine an actual location of the cryoballoon.

13. The electrophysiology system of claim 12, wherein the relative position indicator includes fiducial markers on the cryoballoon catheter and the auxiliary device.

14. The electrophysiology system of claim 12, wherein the cryoablation catheter further comprises a fiducial sensor configured to sense and provide an output indicative of a position of the fiducial markers relative to the fiducial position sensor.

15. The electrophysiology system of claim 14, further comprising a locking element on one or both of the cryoablation catheter and the auxiliary device configured to selectively fix a position of the cryoballoon catheter relative to the auxiliary device.

16. An electrophysiology method comprising:
generating a localization field using a localization field generator;
determining, by a navigation and mapping controller, a sensed device location of a location sensor disposed within the localization field on an auxiliary device operatively coupled to a cryoablation catheter having a cryoballoon at a distal portion of the cryoablation catheter;
determining, by the navigation and mapping controller, a sensed distal shaft end location of a sheath location sensing element within the localization field on a tubular shaft of the cryoablation catheter;
determining a relative position of the cryoballoon relative to the sheath location sensing element and the location sensor based on a relative position indicator on a proximal portion of the cryoablation catheter and a proximal portion of the auxiliary device wherein the relative position applicable to the sensed device location and the sensed distal shaft end location determine an actual location of the cryoballoon; and
generating a graphical representation of the cryoballoon superimposed on a three-dimensional rendering of a cardiac chamber located within the localization field based on the actual location.

17. The method of claim 16, wherein the relative position indicator includes fiducial markers on of the auxiliary device and the cryoablation catheter.

18. The method of claim 17, further comprising locking the position of the cryoablation catheter relative to the auxiliary device using a locking element.

19. The method of claim 17, wherein determining the location of the cryoballoon relative to the location sensor includes sensing a position of the fiducial markers.

* * * * *